(12) United States Patent
Akcay et al.

(10) Patent No.: US 10,543,341 B2
(45) Date of Patent: Jan. 28, 2020

(54) SAFETY CATHETER WITH PASSIVE RELEASE

(71) Applicant: SMITHS MEDICAL ASD, INC., Plymouth, MN (US)

(72) Inventors: Gursel Akcay, Madison, CT (US); Harsh D Chheda, Cheshire, CT (US); David J Goral, Brookfield, CT (US); Thomas T Koehler, Simsbury, CT (US)

(73) Assignee: SMITHS MEDICAL ASD, INC., Madison, CT (US)

( * ) Notice: Subject to any disclaimer, the term of this patent is extended or adjusted under 35 U.S.C. 154(b) by 32 days.

(21) Appl. No.: 16/065,578

(22) PCT Filed: Mar. 21, 2018

(86) PCT No.: PCT/US2018/023550
§ 371 (c)(1),
(2) Date: Jun. 22, 2018

(87) PCT Pub. No.: WO2018/175573
PCT Pub. Date: Sep. 27, 2018

(65) Prior Publication Data
US 2019/0374749 A1     Dec. 12, 2019

Related U.S. Application Data

(60) Provisional application No. 62/475,428, filed on Mar. 23, 2017.

(51) Int. Cl.
*A61M 25/06*     (2006.01)

(52) U.S. Cl.
CPC .... *A61M 25/0618* (2013.01); *A61M 25/0606* (2013.01); *A61M 25/0693* (2013.01)

(58) Field of Classification Search
CPC .......... A61M 25/0618; A61M 25/0606; A61M 25/0693
USPC ..................................................... 604/164.08
See application file for complete search history.

(56) References Cited

U.S. PATENT DOCUMENTS

| | | | |
|---|---|---|---|
| 6,595,954 B1 | 7/2003 | Luther et al. | |
| 8,647,301 B2 | 2/2014 | Bialecki et al. | |
| 2009/0312711 A1* | 12/2009 | Brimhall | A61M 25/0618 604/164.08 |
| 2015/0290430 A1* | 10/2015 | Koehler | A61M 25/0618 604/164.08 |
| 2016/0015941 A1 | 1/2016 | Tanabe et al. | |

OTHER PUBLICATIONS

International Search Report and Written Opinion of the International Searching Authority dated Jun. 1, 2018 in PCT Application No. PCT/US18/23550.

* cited by examiner

*Primary Examiner* — Phillip A Gray
(74) *Attorney, Agent, or Firm* — Snell & Wilmer L.L.P.

(57) ABSTRACT

A safety intravenous catheter that includes a passive release feature. The catheter assembly includes ready, safe, and released positions. In the release position, a retainer being in a proximal retainer position relative to a collar enables release of the catheter hub from the catheter insertion device. The sharp tip of the insertion needle remains inaccessible in the release position in order to prevent unwanted needle sticks.

13 Claims, 6 Drawing Sheets

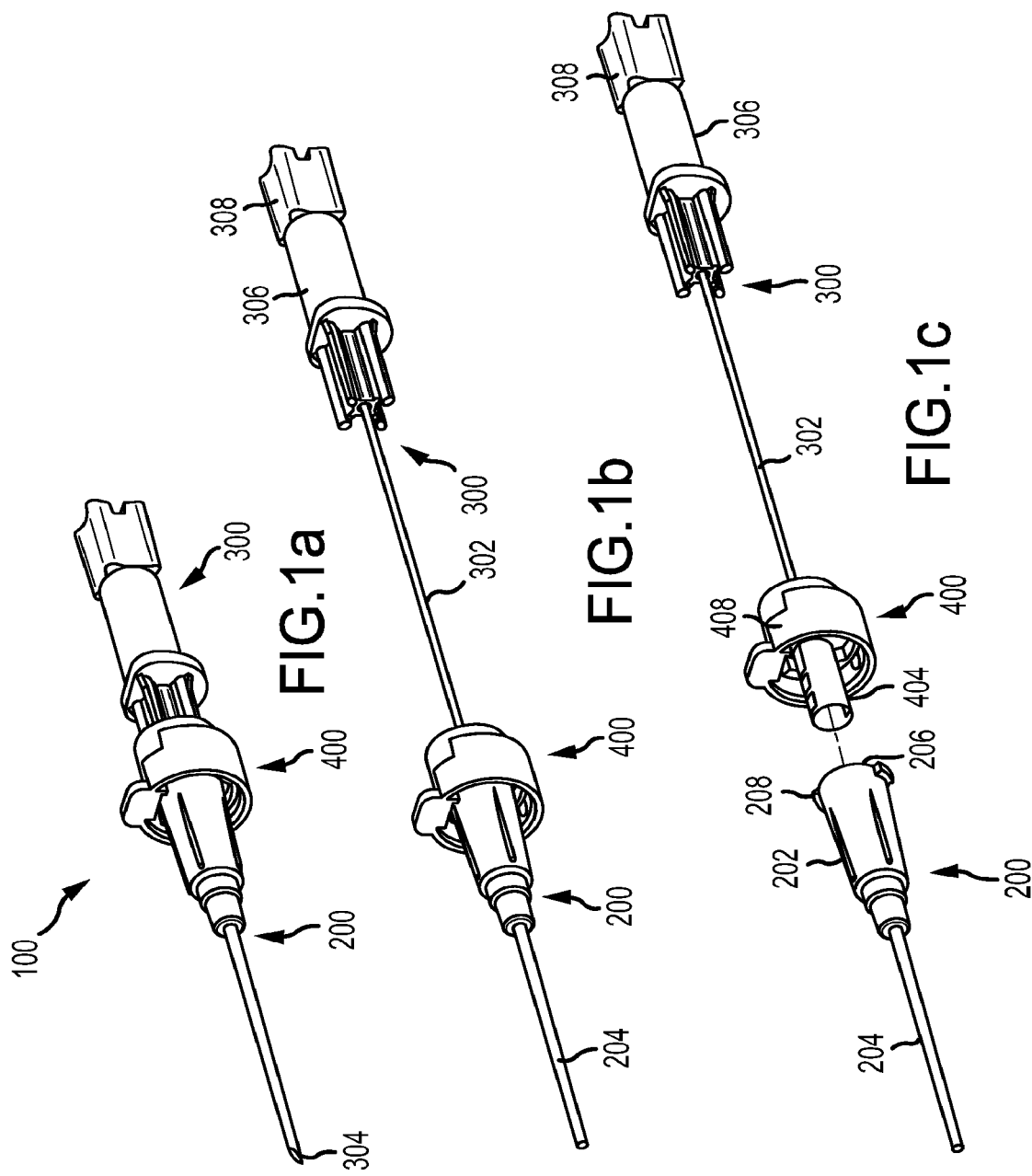

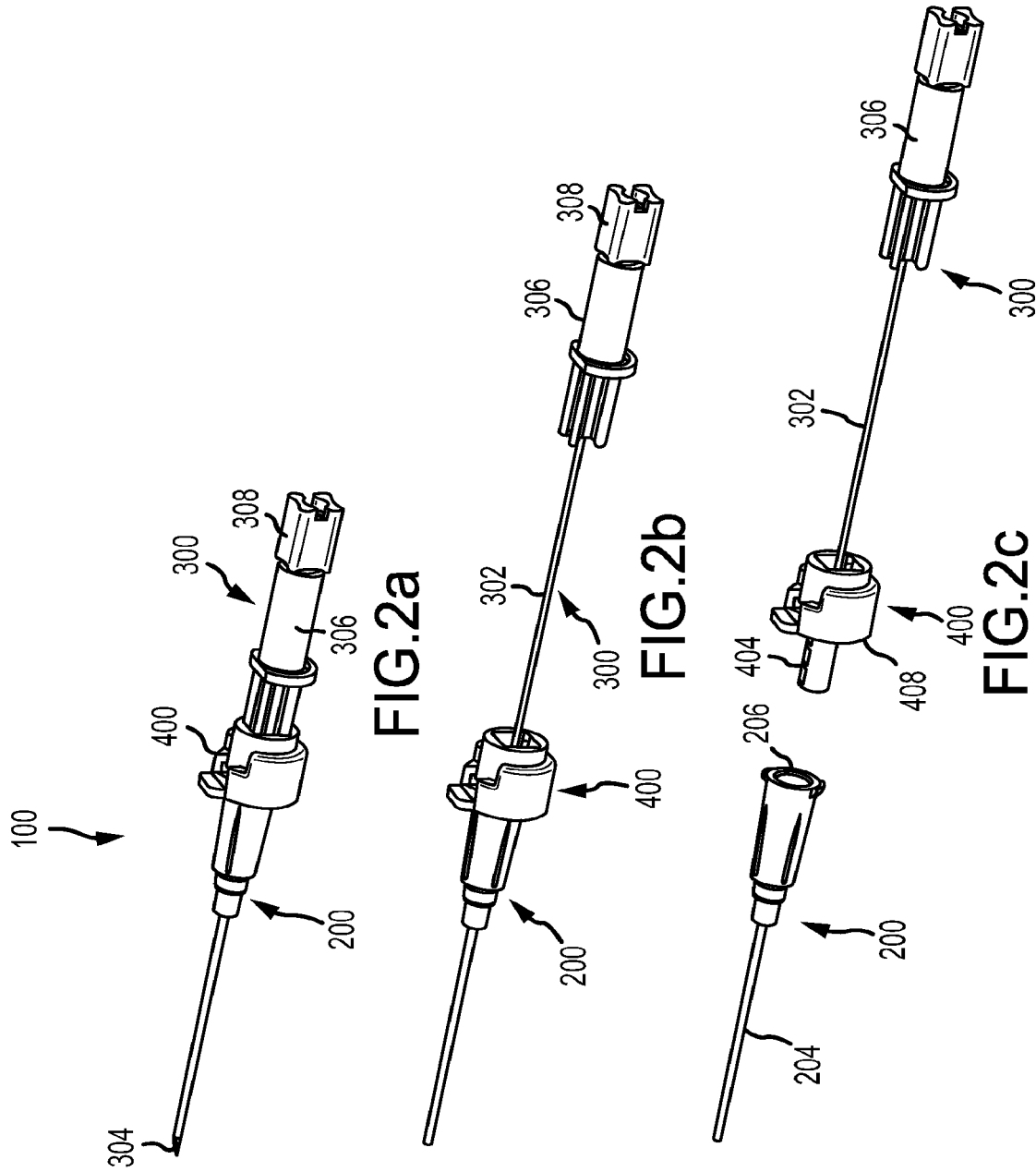

SAFETY CATHETER WITH PASSIVE RELEASE

CROSS-REFERENCE TO RELATED APPLICATIONS

This application is U.S. national phase filing under 35 U.S.C. § 371 of PCT/US2018/23550 (the "550 application") filed on Mar. 21, 2018 and entitled "SAFETY CATHETER WITH PASSIVE RELEASE." The '550 application claims priority from U.S. Ser. No. 62/475,428 filed on Mar. 23, 2017 and entitled "SAFETY CATHETER WITH PASSIVE RELEASE." Both of the aforementioned applications are incorporated herein by reference in their entirety for all purposes.

FIELD

The present disclosure relates to a safety intravenous (IV) catheter and more particularly to a safety IV catheter that includes a passive release feature.

RELATED ART

Safety catheter assemblies typically include a catheter and a catheter insertion device having an insertion needle. The catheter is provided assembled to the catheter insertion device in a ready for use configuration with a tube of the catheter positioned over the insertion needle and a sharp tip of the insertion needle protruding from a distal end of the catheter. A needle sheath may be positioned over the sharp tip of the insertion needed to prevent unwanted needle sticks prior to the catheter assembly being used. The overall safety catheter assembly, including the catheter, catheter insertion device, and needle sheath, may be provided for use in a sterilized and assembled state, contained within a sealed package. One example of such a safety catheter includes the JELCO INTUITIV (Trademark) safety catheter marketed by Smiths Medical ASD, Inc. of Plymouth, Minn., as described in U.S. Pat. No. 8,257,322.

To insert the catheter into the vein of a subject, a clinician first removes the safety catheter assembly from the packaging. The needle sheath is removed to expose the sharp tip of the insertion needle that is protruding from the distal end of the catheter. The clinician punctures an identified site of a subject with the sharp needle tip and urges the insertion needle forward until the needle tip enters the vein of the subject. An initial amount of blood may pass through a lumen of the needle, entering the catheter and/or catheter insertion device where the clinician may view the "flashback" of the blood to confirm entry into the vein. The catheter may then be moved distally over the needle to thread the tube of the catheter into position in the vein of the subject. The needle may be held stationary during catheter threading. With the catheter positioned as desired, the clinician withdraws the needle by pulling the catheter insertion device proximally away from the subject while holding the catheter generally stationary with respect to the subject. The needle assembly is pulled proximally until the needle and catheter insertion device are separated from the catheter. The clinician may dispose of the catheter insertion device in a sharps container, after the insertion device is separated from the catheter.

BRIEF DESCRIPTION OF THE FIGURES

FIGS. 1a-1c are perspective views, taken from a distal vantage, of an example embodiment of a safety catheter assembly in each of a ready position (FIG. 1a), a safe position (FIG. 1b) and a release position (FIG. 1c).

FIGS. 2a-2c are perspective views, taken from a proximal vantage, of the safety catheter assembly of FIGS. 1a-1c in each of a ready position (FIG. 2a), a safe position (FIG. 2b) and a release position (FIG. 2c).

DETAILED DESCRIPTION

Figure 3A:
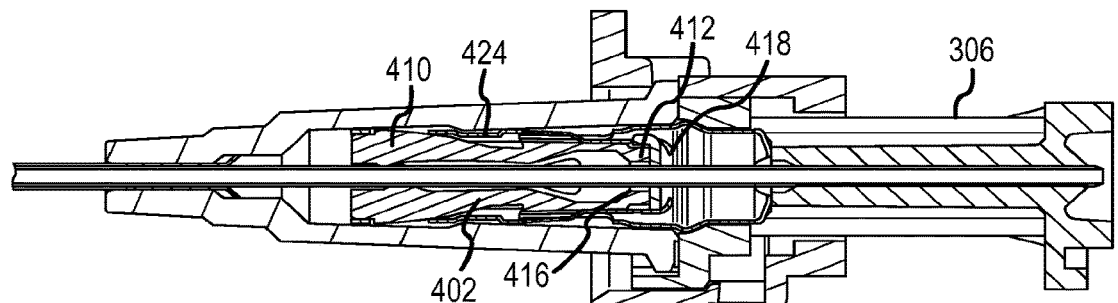
FIGS. 3a-3d are cross section views of the safety catheter assembly of FIGS. 1a-2c in each of a ready position (FIG. 3a), a safe position (FIG. 3b) and a release position (FIGS. 3c and 3d).

Safety catheter assemblies, according to various example embodiments disclosed herein, may be positioned during use in a ready for use position, a safe and engaged position, and a safe and released position. In the ready for use (equivalently referred to herein as the "ready position"), the catheter is assembled to the catheter insertion device with the sharp tip of the needle protruding from a distal end of the catheter tube and the catheter hub secured to the catheter insertion device in a manner that prevents removal therefrom. In the safe and engaged position (equivalently referred to herein as the "safe position") the sharp tip of the insertion needle is positioned internally to a tip protector of the catheter insertion device in order to prevent access to the needle that might otherwise result in unwanted needle sticks. The catheter remains secured to the catheter insertion device when in the safe and engaged position. In the safe and released position (equivalently referred to herein as the "release position") the catheter is disengaged from the catheter insertion device so that the insertion device may be separated from the catheter and disposed of in a safe manner. The sharp tip of the insertion needle remains inaccessible in the release position in order to prevent unwanted needle sticks.

Turn now to the figures, and initially FIGS. 1a to 3d, which show an example embodiment of a safety catheter assembly 100 that includes a catheter 200, an insertion needle assembly 300, and a needle tip protector assembly 400. The catheter 200, insertion needle assembly 300, and needle tip protector assembly 400 are shown in each of the ready position (FIGS. 1a, 2a, and 3a), the safe position (FIGS. 1b, 2b, and 3b), and the release position (FIGS. 1c, 2c, 3c, and 3d), according to one example embodiment. As may be appreciated, FIGS. 1a-1c and 2a-2c show the safety catheter assembly 100 in a perspective view taken from distal and proximal vantages, respectively. FIGS. 3a-3d are cross sectional views of a portion of the catheter assembly.

The catheter includes a catheter hub 202 and a catheter tube 204 that cooperate to provide a fluid pathway to the vein of a subject and other IV fluid components, such as an IV fluid supply. The catheter tube 204 includes a distal end, a proximal end, and a lumen extending therebetween. The proximal end of the catheter tube 204 is connected to a distal portion of the catheter hub 202. A proximal end 206 of the catheter hub is constructed and arranged to connect to other IV fluid components and may be designed in accordance with ISO standards, according to some embodiments. In the illustrated example embodiment, the proximal end of the catheter hub includes luer lugs, although other constructions are also contemplated.

The insertion needle assembly 300 includes an insertion needle 302 having a sharp tip 304 that may create an entry passageway into the vein of a subject. The insertion needle extends from a sharp distal tip 304 to a proximal portion that is connected to a needle hub 306, and defines an internal lumen that extends therebetween. The proximal portion of the insertion needle is connected to and in fluid communication with the needle hub 306. The needle hub, in turn, is connected to the flash plug 308 to allow blood to flow from the needle tip to the flash plug. The flash plug may 308 include a microporous barrier that permits the escape of air but prevents the escape of fluid. The body of the insertion needle may include a transition or bump 310 that interacts with the needle tip protector to move the catheter assembly between the ready, safe, and released positions, according to some embodiments.

The illustrated example embodiment also includes a needle tip protector. The tip protector 400 includes an inner member 402, an outer member 404, a retainer 406, and a collar 408, each of which is shown separately in FIGS. 5 to 8. The inner member 402 and the outer member 404 of the tip protector cooperate to prevent access to the needle tip 304 in the safe and released positions. Additionally, the retainer 406 and the collar 408 cooperate to secure the catheter 200 to the tip protector assembly 400 in each of the ready and safe positions, while enabling release of the catheter in the release position.

The transition or bump 310 on the body of the needle 302 acts move the tip protector 400 between the ready, safe, and release positions and may also prevent separation of the insertion needle assembly 300 from the tip protector assembly 400. The inner member 402 of the tip protector 404 includes distal arms 410, a proximal base 412, and a bump washer 414. The bump washer 414 defines a proximal needle stop 416 and a proximal opening 418 that allows passage of the needle 302 but not the bump 310. When the insertion needle 302 is pulled proximally between the ready and safe positions, the transition 310 contacts the proximal needle stop 416 to prevent the transition 310 from passing through the proximal opening 418, thus preventing separation of the insertion needle assembly 300 from the tip protector 400.

In the illustrated embodiment, the proximal needle stop 416 is formed in a bump washer 414 that is assembled to the proximal end of the inner member 402. The bump washer 414 is shaped generally like a traditional washer with the inclusion of a distally extending arm 420 that facilitates connection to other portions of the inner member. The bump washer may be made of a rigid material, such as a metal or plastic that resists deformation when contacted by the transition of the insertion needle. It is to be appreciated that proximal stops, according to alternate example embodiments, may be formed directly in the retainer or in different types of bump washers, such as bump washers that lack a distally extending tab or that are made of materials other than metal.

The transition 310 may be located on the needle 302 so that the needle tip 304 is positioned within the inner member 402 of the tip protector 400 when the transition contacts the proximal stop 416, such that access to the needle tip may be prevented. This may generally be accomplished by locating the transition 310 a distance from the needle tip 304 that is less than the distance between the proximal stop 416 and the distal end 422 of the inner member 402. According to some embodiments, the distance between the transition and the needle tip may be smaller than a distance between the proximal stop and a distal stop on the inner member. It is to be appreciated, however, that other configurations are possible, including embodiments where the transition is located on the needle such that the needle tip is positioned internally to the outer member or another component of the tip protector.

Figure 3B:
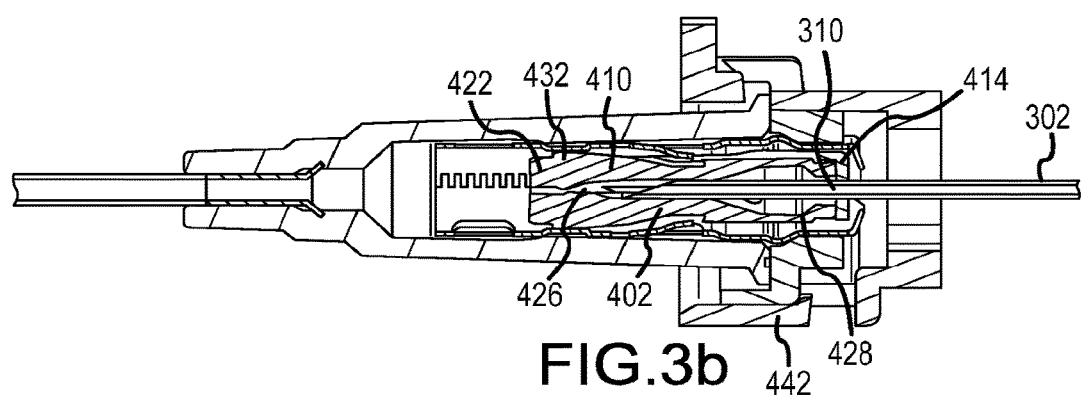

Further proximal movement of the insertion needle 302, once the transition 310 is in contact with the proximal stop 416, causes the inner member 402 to move proximally relative to the outer member 404 from a distal inner member position to a proximal inner member position, as may be seen in the progression of movement between FIGS. 3a and 3b. Movement of the inner member 402 within the outer member 404 causes arms 410 of the inner member to move into a restriction 424 of the outer member. Interaction between the arms 410 and the outer member 424 urges the arms toward one another, causes the arms to form a distal needle stop 426 in the passageway previously occupied by the insertion needle 302. The distal needle stop 426 prevents distal movement of the needle from outside of the interior of the inner member, and thus protects clinicians and others from the sharp needle tip.

The arms of the inner member may include protrusions or ribs that engage one another to form the distal needle stop when the inner member is in the proximal inner member position, such as when the tip protector assembly is in either of the safe or release positions. These or other features of the arms may contact one another, fully occupying the needle passageway to form the distal needle stop, as shown in FIG. 3b. It is to be appreciated, however, that other embodiments may lack such fingers or ribs. It is also to be appreciated that the distal needle stop may not fully occupy the needle passageway when in the safe position, according to alternate embodiments. In one such alternate embodiment, the arms of the inner member are urged toward one another to form a distal needle stop that restricts passage of the sharp needle tip without fully occupying the needle passageway.

The distal arms 410 of the inner member may be biased in the radially outward direction, away from one another. Such a bias may promote separation of the distal arms 410 from one another and thus from the insertion needle 302 prior to the needle reaching the safe position. Such separation may minimize friction between the insertion needle 302 and inner member 402, promoting easy movement of the insertion needle from the ready position to the safe position. According to some embodiments, the inner member is made of a resilient rubber or plastic material.

The distal arms 410 may include a hinge area 428 near a connection to the proximal base 412 and an enlarged distal portion 430. The hinge area may promote flexing of the distal arms between the ready position and the safe position. The enlarged distal portions 430 may be shaped and sized to form the distal needle stop 426 when moved inwards or toward one another by the restriction 424 of the outer member. In the illustrated embodiment, the distal portion of at least one of the arms includes a ramp structure 432 that interacts with the outer member 404 to urge the arm inward 410, toward the needle passageway, as the inner member is pulled proximally by movement of the insertion needle.

The inner member includes a safe position lock 434 that prevents distal movement of the inner member, once in the inner member proximal position relative to the outer member. In the illustrated example embodiment, the lock 434 includes a distally facing inner member lock surface 436 that interacts with an inwardly biased tab 438 of the outer member 404. Proximal movement of the inner member 402 brings the lock surface into engagement with a proximally facing lock surface of the tab 438. Once engaged, the lock surfaces 436 of the inner member 402 and the tab 438 prevent emergence of the needle tip 304 by preventing the inner member 402 from returning to the distal inner member position. It is to be appreciated that the safe position lock shown in the illustrated example embodiment is but one type of lock and that others are also contemplated.

As may be seen in FIGS. 3a and 3b, in each of the ready and safe positions the catheter 200 is secured to the needle tip protector 400 in a manner that prevents separation, with the retainer 406 in a distal retainer position relative to the collar 408. This is accomplished by various engagement features in the needle tip protector 400 that secure the catheter 200 to the tip protector until the tip protector is in the release position. In the illustrated embodiment, external engagement features are located on the collar and the retainer. The outer member may additionally provide internal engagement features that help to secure the catheter to the tip protector.

The collar 408 includes a notch 440 that receives a first luer lug 208 of the catheter hub 202. The notch 440 engages a forward facing surface of the luer lug to prevent the lug and thus the catheter from moving distally away from the tip protector assembly. Contact between a notch and the first luer lug of the catheter may also prevent the catheter hub from moving laterally away from the tip protector.

External engagement features are provided by the retainer, in the illustrated example embodiment. The retainer includes a base and a lateral wall that form a pocket that receives the proximal end of the catheter hub. Inner portions of the catheter wall engage corresponding outer surfaces of the catheter hub to secure the catheter to the tip protector assembly. Although the retainer is shown to have a pocket with a shape that corresponds to that of the proximal end of the catheter, it is to be appreciated that other configurations are also contemplated, such as configurations that engage the second luer lug of the catheter hub.

The outer member of the needle tip protector assembly may, according to some embodiments, contact the interior of the catheter hub to provide an interior engagement. By way of example, the outer member may be sized such that a sliding surface of the outer wall makes contact with the interior of the catheter hub. This contact may prevent the catheter hub from moving laterally with respect to the outer member and other portions of the tip protector without directly preventing distal movement of the catheter. According to other embodiments, the outer member may be shaped and sized such that there is no contact between the outer member and the catheter hub.

With the tip protector assembly in the safe position and the inner member in contact with the proximal wall of the outer member, further proximal movement of the insertion needle causes the retainer, and other components of the tip protector, to move proximally relative to the collar to a proximal retainer position. This motion causes external engagement features of the retainer to move proximally away from the corresponding outer surfaces of the catheter hub, as shown in the progression of movement between FIGS. 3b and 3c. The sliding surface of the outer member is also moved proximally and out of contact with the inner surface of the catheter hub, at least in embodiments that include contact between the catheter hub and inner member.

The tip protector may include a feature that resists proximal movement of the retainer to the proximal release position prior to being in the safe position. The illustrated example embodiment includes a retention finger that is integrated into the collar and that includes a spring arm and a retention tab. The retention tab is positioned proximally to the retainer. Proximal movement of the retainer is resisted by the retention tab, until the forces associated with flexing the spring arm and retention tab away from the retainer are overcome. In this respect, the retention tab 442 of the collar 408 provides a release threshold force that is to be overcome prior to the catheter 200 being released from the tip protection assembly 400.

The release threshold force may be higher than the forces associated with movement from the ready position to the safe position (i.e., the safety threshold force), according to some embodiments. Having the release threshold force higher than the safe threshold force may prevent the catheter from being released prior to the tip protection assembly being moved to the safe position. The release threshold force, according to some embodiments, is more than 2× the safety threshold force, more than 3× the safety threshold force, or more than 5× the safety threshold force.

Figure 3C:
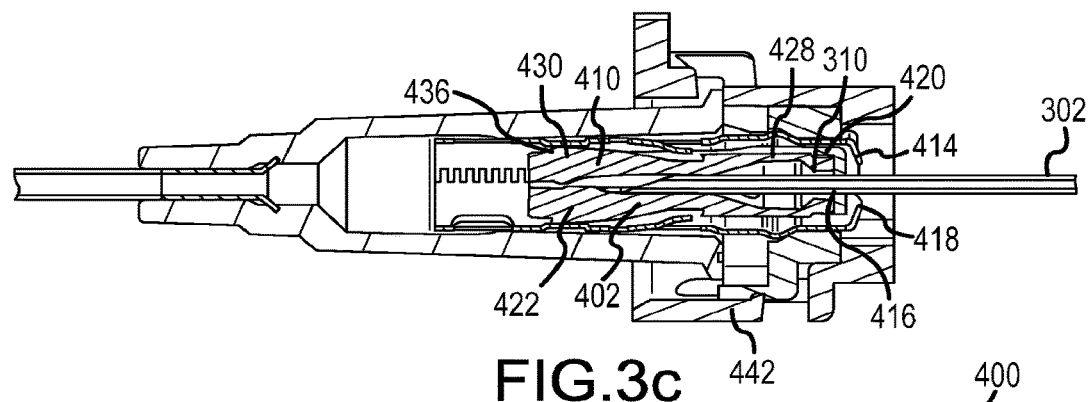
Figure 3D:
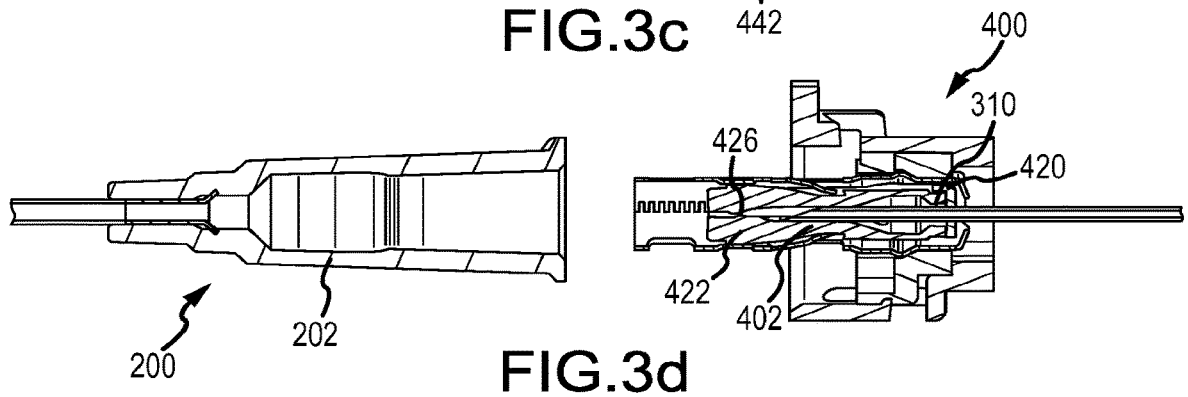
Figure 4A:
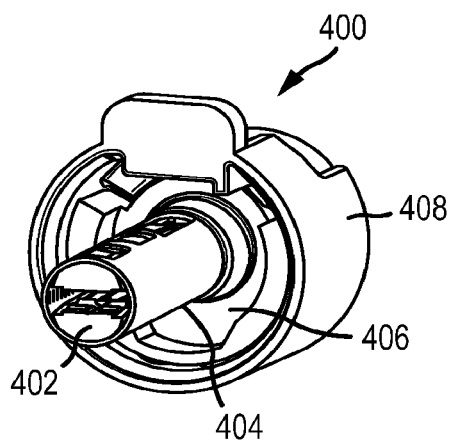
FIGS. 4a-4c are perspective views, taken from a distal vantage, of the tip protector assembly of FIGS. 1a-3d in each of a ready position (FIG. 4a), a safe position (FIG. 4b) and a release position (FIG. 4c). The catheter and needle are removed from FIGS. 4a-4c for purposes of illustration.
Figure 4B:
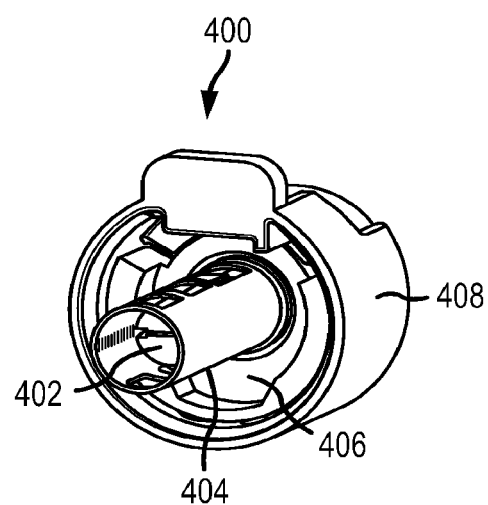
Figure 4C:
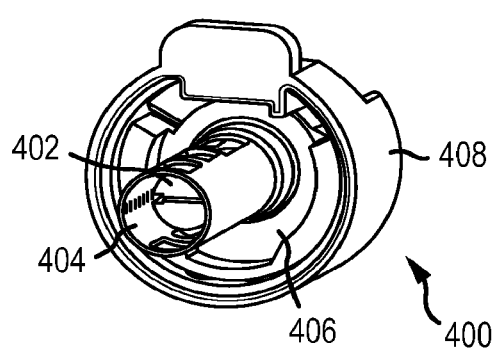
Figure 5:
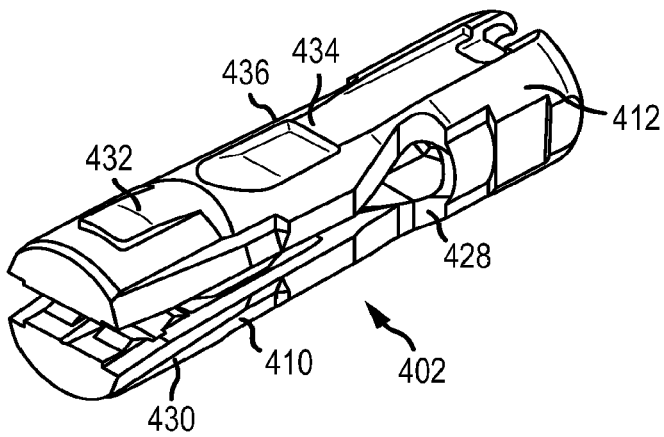
FIG. 5 is a perspective view of an inner member of a tip protector assembly, according to one example embodiment.
Figure 7:
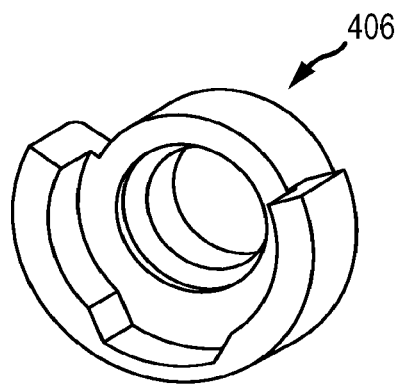
FIG. 7 is a perspective view of a retainer of a tip protector assembly, according to one example embodiment.
Figure 6:
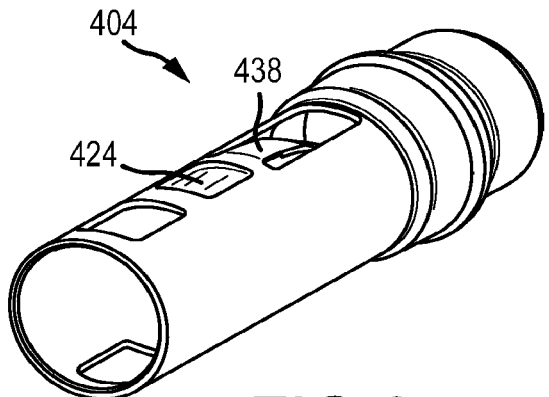
FIG. 6 is a perspective view of an outer member of a tip protector assembly, according to one example embodiment.
Figure 8:
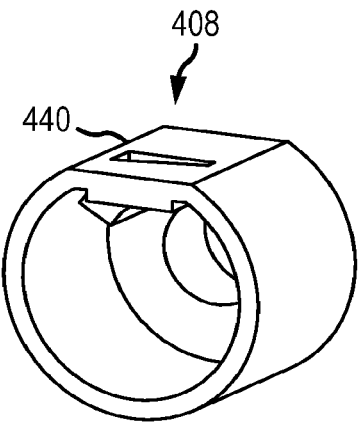
FIG. 8 is a perspective view of a collar of a tip protector assembly, according to one example embodiment.

The catheter hub 202 is released from secure connection to the tip protection assembly 400 when the external engagement features of the retainer 406 are out of engagement with the catheter hub 202, as shown in FIG. 3c. In this position, the further proximal movement of the insertion needle assembly 300 will pull the needle tip protector 400 away from the catheter hub 202, as reflect in FIG. 3d. Separation of the collar 408 from the catheter hub 202 may be accompanied by a slight jogging of the tip protector in a lateral direction, away from the needle passage, according to some embodiments. The sloped shape of the luer lug and/or the notch may promote this motion. Additionally or alternately, the clinician may tilt pull on the insertion needle assembly at an upward angle to promote separation of the catheter from the collar.

Figure 9:
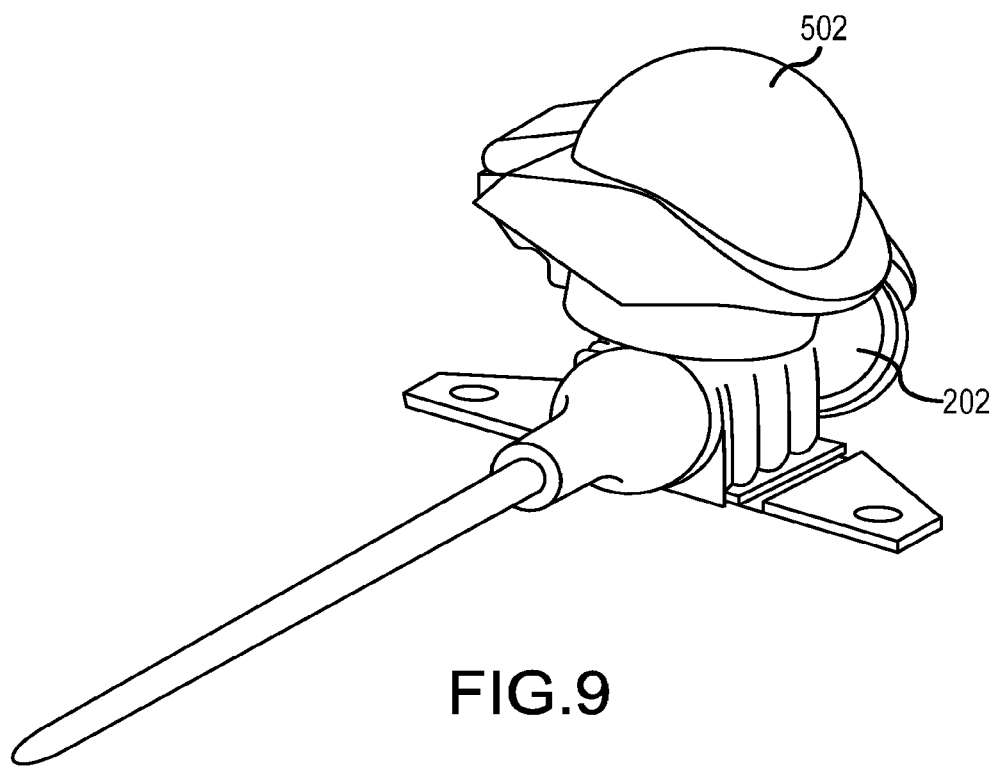
FIG. 9 is a perspective view of a catheter hub that includes a side port, according to one example embodiment.
Figure 10:
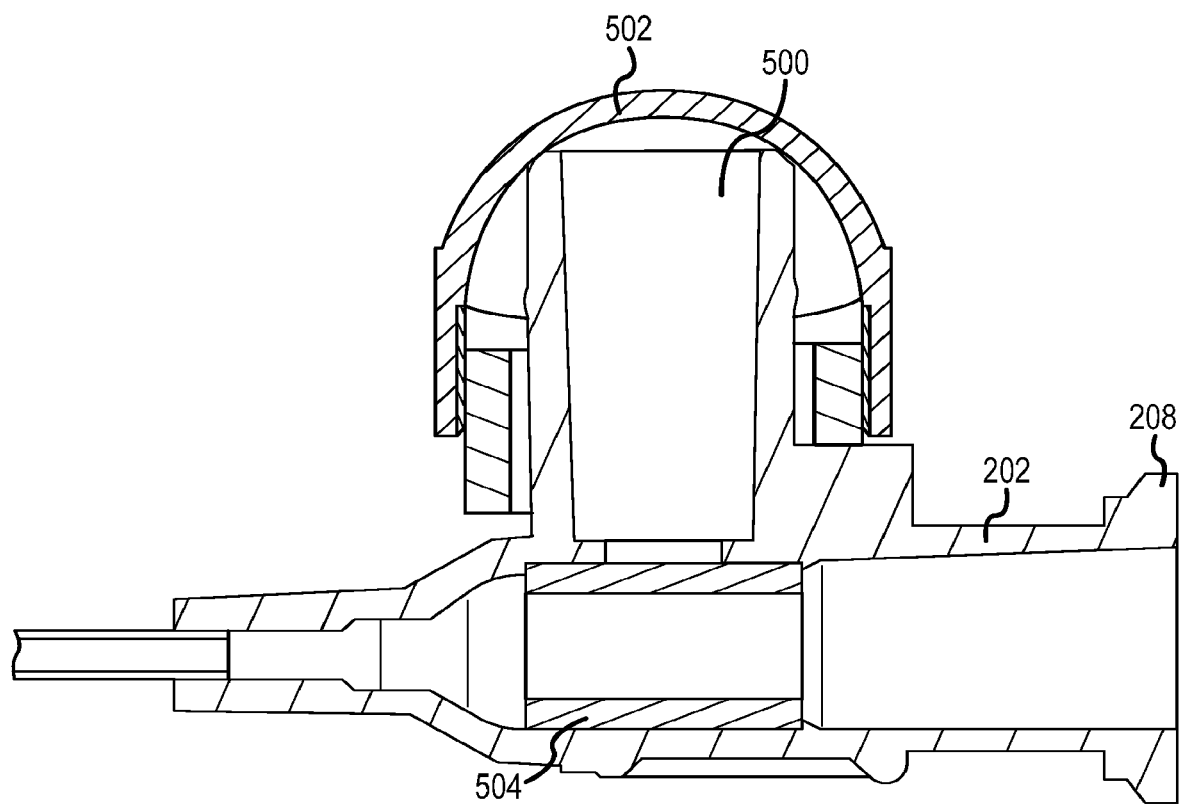
FIG. 10 is a cross sectional view of the catheter hub shown in FIG. 9, along a vertical plane that lies along the needle axis.

The catheter hub may include a side port 500, such as in the example embodiment of FIGS. 9 and 10. As shown, the catheter hub 202 includes a side port that may be accessed through a lateral, luer type connection that is integrated into the catheter hub. A side port cap 502 may be selectively positioned over the side port to close and open access thereto, as desired. A flexible, cylindrically shaped septum is positioned internally to the catheter hub. The septum 504 is moved away from the side port by pressurized fluid that is introduced into the luer to allow the pressurized fluid to enter the catheter hub. In the absence of pressurized fluid in the luer, the septum closes access to the side port to prevent the escape of fluids from the catheter.

Various example embodiments of catheters are described herein for use in accessing the vein of a subject. It is to be appreciated, however, that the example embodiments described herein may alternately be used to access the vasculature of a subject at locations other than a vein, including but not limited to the artery of a subject. It is additionally to be appreciated that the term "clinician" refers to any individual that may be performing a catheter insertion procedure with any of the example embodiments described herein or combinations thereof. Similarly, the term "subject", as used herein, is to be understood to refer to an individual or object in which a catheter is to be inserted, whether human, animal, or inanimate. Various descriptions are made herein, for the sake of convenience, with respect to procedures being performed by a clinician to access the vein of a subject, while the disclosure is not limited in this respect.

It is also to be appreciated that the term "distal", as used herein, refers to the direction, taking along an axis that lies parallel to the needle of a safety catheter assembly that is closest to a subject during catheter insertion. Conversely, the term "proximal", as used herein, refers the direction lying along the axis parallel to the needle that is farther away from the subject when the catheter is inserted into the vein of the subject—that is, opposite to the distal direction.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future-filed applications claiming priority to this application may claim the disclosed subject matter in a different manner and generally may include any set of one or more features as variously disclosed or otherwise demonstrated herein.

What is claimed is:

1. A safety catheter comprising:
   a catheter including a catheter tube and a catheter hub;
   a catheter insertion device including an insertion needle and a tip protector assembly that is operably connected to the insertion needle, the insertion needle having a sharp tip, a needle transition spaced from the sharp tip by a transition distance and a proximal end, the tip protector assembly having an inner member, an outer member, a retainer, and a collar, with the inner member being movable between a distal inner member position and a proximal inner member position relative to the outer member and the retainer being movable between a distal retainer position and a proximal retainer position relative to the collar, the tip protector assembly movable between three operating positions including a ready position, a safe position, and a release position,
   wherein in the ready position, at least a portion of the insertion needle is positioned inside of the catheter tube, the inner member being in the distal inner member position relative to the outer member, the retainer being in the distal retainer position relative to the collar with the retainer and collar engaging the catheter hub to prevent release of the catheter hub from the catheter insertion device;
   wherein in the safe position, the inner member is in the proximal inner member position relative to the outer member with the sharp tip of the insertion needle positioned internally to the tip protector assembly, the retainer being in the distal retainer position relative to the collar with the retainer and collar engaging the catheter hub to prevent release of the catheter hub from the catheter insertion device; and
   wherein in the release position, the inner member is in the proximal inner member position relative to the outer member with the sharp tip of the insertion needle positioned internally to the tip protector assembly and the retainer being in the proximal retainer position relative to the collar to enable release of the catheter hub from the catheter insertion device.

2. The safety catheter of claim 1, wherein the tip protector assembly moves from the ready position to the safe position and then, afterwards, to the release position during insertion needle withdrawal from the catheter.

3. The safety catheter of claim 2, wherein interaction between the needle transition and a proximal stop of the inner member during insertion needle withdrawal causes the inner member to move from the distal inner member position to the proximal inner member position relative to the outer member to place the tip protector assembly in the safe position.

4. The safety catheter of claim 3, wherein, after the inner member reaches the proximal inner member position, further insertion needle withdrawal causes the needle transition to move the retainer from the retainer distal retainer position to the proximal retainer position relative to the collar to place the tip protector assembly in the release position.

5. The safety catheter of claim 4, wherein the inner member has a length between a distal end of the inner member and the proximal stop that is greater than the transition distance.

6. The safety catheter of claim 5, wherein the inner member includes a safe position lock that prevents distal movement relative to the outer member once the inner member is in the inner member proximal position.

7. The safety catheter of claim 6, wherein the inner member includes a metal washer that prevents proximal passage of the transition and the sharp tip from tip protector assembly and arms that move radially inward when the inner member is in the proximal inner member position to provide a distal stop that prevents distal movement of the sharp tip from the tip protector assembly.

8. The safety catheter of claim 7, wherein the catheter hub is retained to the tip protector assembly at least by engagement between external engagement features of the catheter hub and the collar and the retainer when the tip protector assembly is in the safe position and wherein movement of the retainer to the proximal retainer position enables release of the catheter from the tip protector assembly.

9. The safety catheter of claim 8, wherein the retainer is fixedly connected to the outer member and the outer member moves with the retainer from the distal retainer position to the proximal retainer position.

10. The safety catheter of claim 9, wherein the catheter hub is further retained to the tip protector assembly by engagement between inner portions of the catheter hub and the outer member when the tip protector assembly is in the safe position.

11. The safety catheter of claim 3, wherein movement of the tip protector assembly from the ready position to the safe position is associated with exceeding safety threshold force during needle withdrawal and further wherein movement of the tip protector assembly from the safe position to the release position is associated with exceeding a release threshold force during needle withdrawal, the release threshold force being greater than the safety threshold force.

12. The safety catheter of claim 11, wherein the collar includes a retention finger that resists movement of the retainer to the proximal retainer position.

13. The safety catheter of claim 1, wherein the catheter further comprises a side port.

* * * * *

UNITED STATES PATENT AND TRADEMARK OFFICE
CERTIFICATE OF CORRECTION

PATENT NO. : 10,543,341 B2
APPLICATION NO. : 16/065578
DATED : January 28, 2020
INVENTOR(S) : Gursel Akcay et al.

Page 1 of 1

It is certified that error appears in the above-identified patent and that said Letters Patent is hereby corrected as shown below:

On the Title Page

Item (73), delete Assignee City/State "Madison, CT" and therefore insert correct Assignee City/State --Plymouth, MN.--

Signed and Sealed this
Twenty-eighth Day of July, 2020

Andrei Iancu
*Director of the United States Patent and Trademark Office*